United States Patent
Li et al.

(10) Patent No.: US 6,773,888 B2
(45) Date of Patent: Aug. 10, 2004

(54) PHOTOACTIVATABLE SILANE COMPOUNDS AND METHODS FOR THEIR SYNTHESIS AND USE

(75) Inventors: Handong Li, San Jose, CA (US); Glenn McGall, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/192,598

(22) Filed: Jul. 9, 2002

(65) Prior Publication Data

US 2003/0194715 A1 Oct. 16, 2003

Related U.S. Application Data (60) Provisional application No. 60/371,049, filed on Apr. 8, 2002.

(51) Int. Cl.[7] .............................. C12Q 1/68; C07H 21/00
(52) U.S. Cl. ........................................... 435/6; 536/23.1
(58) Field of Search .............................. 536/23.1; 435/6

(56) References Cited

U.S. PATENT DOCUMENTS 5,773,308 A * 6/1998 Conrad et al. .............. 436/527
5,919,523 A * 7/1999 Sundbert et al. ............ 427/333

OTHER PUBLICATIONS

Prucker et al., *J. Am. Chem. Soc.* 121:8766 (1999).
Handong Li and Glenn McGall, 224th ACS National Meeting Presentation, Boston, Aug. 18–22, 2002.

* cited by examiner

*Primary Examiner*—Jezia Riley
(74) *Attorney, Agent, or Firm*—Thomas E. Malone; Philip L. McGarrigle (57) ABSTRACT

In one aspect of the invention, photoactivatable silane compounds and methods for their synthesis and use are provided. In one embodiment, the photoactivatable silane compounds synthesized are represented by a formula: PG-LS-SN, wherein PG is a photoactivatable group, LS is a linkage and spacer group, and SN is a silane group. The silanes allow the photoactivatable silane compounds to be covalently bound to the surface of a substrate such as silica. The photoactivatable group forms a hydrophobic layer that can be photochemically cross-linked with a layer of hydrophilic functional polymers. In another embodiment, a method is disclosed to synthesize a substrate of hydrophobic layers and hydrophilic functional polymer layers thereafter onto glass surfaces. An array of biopolymers such as nucleic acids and peptides may then be covalently attached to the substrate using photolithography and biopolymer synthesis.

45 Claims, 8 Drawing Sheets

Poly-HEAA

Poly-HEAA-MAA

Figure 7

11 atoms 13 atoms 17 atoms 19 atoms

PHOTOACTIVATABLE SILANE COMPOUNDS AND METHODS FOR THEIR SYNTHESIS AND USE

CROSS REFERENCE TO RELATED APPLICATIONS

This application claims the benefit of U.S. Provisional Application Serial No. 60/371,049, filed Apr. 8, 2002, the disclosure of which is incorporated herein by reference in its entirety.

TECHNICAL FIELD

This application relates to photoactivatable silane compounds, methods of making photoactivatable silane compounds, and methods for use of photoactivatable silane compounds as silylating agents in the treatment of surfaces, such as glass.

BACKGROUND OF THE INVENTION

Silylating agents have been developed in the art which react with and coat surfaces, such as silica surfaces. For example, silylating agents for use in modifying silica used in high performance chromatography packings have been developed. Monofunctional silylating agents have been used to form monolayer surface coatings, while di- and tri-functional silylating agents have been used to form polymerized coatings on silica surfaces. Many silylating agents, however, produce coatings with undesirable properties including instability to hydrolysis and the inadequate ability to mask the silica surface which may contain residual acidic silanols.

Recently, a method has been reported for grafting polystrene films to glass surfaces using a photoactivatable silane. Prucker et al., *J. Am. Chem. Soc.* 121:8766 (1999). The system is based on a photoreactive benzophenone derivative that is bound to $SiO_2$ surfaces via a silane anchor.

SUMMARY OF THE INVENTION

In one aspect of the invention, photoactivatable silane compounds and methods for their synthesis and use are provided. In one embodiment, the photoactivatable silane compounds synthesized are represented by a structural formula: PG-LS-SN, wherein PG is a photoactivatable group, LS is a linkage and spacer group, and SN is a silane group. The silanes allow the photoactivatable silane compounds to be covalently bound to the surface of a substrate such as silica. A linkage and spacer joins the silane to the photoactivatable group. The photoactivatable group forms a hydrophobic layer that can be photochemically cross-linked with a layer of hydrophilic functional polymers.

In another embodiment, a method is disclosed to synthesize a substrate of hydrophobic layers and hydrophilic functional polymer layers thereafter onto glass surfaces. The photoactivatable silane compounds are synthesized and bound to the surface of a substrate such as silica. Hydrophilic polymers with reactive functional groups are applied to the substrate, and then photochemically cross-linked to the hydrophobic layers to form a functionalized surface with a plurality of functional groups on the polymer.

In yet another embodiment, after forming of a functionalized surface on the surface of a substrate, an array of biopolymers such as nucleic acids may be covalently attached to the substrate using photolithography and DNA synthesis. The method permits the formation of high density arrays of nucleic acids immobilized on a substrate, which may be used, for example, in conducting high volume nucleic acid hybridization assays.

In a further embodiment, a benzophenone-based silane is synthesized and used to prepare stable, hydrophobic, photoactivatable coatings on solid supports. Hydrophilic polymers are then applied to the substrate, and photochemically cross-linked to the underlying silane. The resulting substrates are suitable for fabricating oligonucleotide probe arrays either by in situ synthesis or immobilization methods.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Silylating agents have been developed for the silylation of solid substrates, such as glass substrates, that include functional groups that may be derivatized by further covalent reaction. The silylating agents have been immobilized on the surface of substrates, such as glass, and used to prepare high density immobilized oligonucleotide probe arrays. For example, N-(3-(triethoxysilyl)-propyl)-4-hydroxybutyramide (PCR Inc., Gainesville, Fla. and Gelest, Tullytown, Pa.) has been used to silylate a glass substrate prior to photochemical synthesis of arrays of oligonucleotides on the substrate, as described in McGall et al., *J. Am. Chem. Soc.*, 119:5081–5090 (1997), the disclosure of which is incorporated herein by reference.

Hydroxyalkylsilyl compounds have been used to prepare hydroxyalkylated substances, such as glass substrates. N,N-bis(hydroxyethyl) aminopropyl-triethoxysilane has been used to treat glass substrates to permit the synthesis of high-density oligonucleotide arrays. McGall et al., *Proc. Natl. Acad. Sci.*, 93:13555–13560 (1996); and Pease et al, *Proc. Natl. Acad. Sci.*, 91:5022–5026 (1994), the disclosures of which are incorporated herein. Acetoxypropyl-triethoxysilane has been used to treat glass substrates to prepare them for oligonucleotide array synthesis, as described in PCT WO 97/39151, the disclosure of which is incorporated herein. 3-Glycidoxy propyltrimethoxysilane has been used to treat a glass support to provide a linker for the synthesis of oligonucleotides. EP Patent Application No. 89 120696.3.

Methods have been developed in the art for stabilizing surface bonded silicon compounds. The use of sterically hindered silylating agents is described in Kirkland et al., *Anal. Chem.* 61: 2–11 (1989); and Schneider et al., *Synthesis*, 1027–1031 (1990). However, the use of these surface bonded silylating agents is disadvantageous, because they typically require very forcing conditions to achieve bonding to the glass, since their hindered nature makes them less reactive with the substrate.

In one aspect of the invention, photoactivatable silane compounds are provided that form a hydrophobic coating offering protection from unwanted hydrolysis and thus increased coating stability. In another aspect of the invention, photoactivatable silane compounds are provided that allow polymer grafting providing multiple points of attachment to the substrate, which further increases the stability of the coating. In yet another aspect, this invention provides higher functional group density by using polymers with a plurality of functional groups. The polymer structure can be specifically designed to provide suitable environment for particular biological interactions.

The photoactivatable silane compounds can be represented by a structural formula I:

PG-LS-SN    I.

In structural formula I, PG is a photoactivatable group, LS is a linkage and spacer group, and SN is a silane group.

In a preferred embodiment, PG is selected from the group, Structure II, consisting of:

In another preferred embodiment, LS is selected from the group, Structure III, consisting of hydrocarbon chains and:

In yet another preferred embodiment, SN is selected from the group, Structure IV, consisting of:

wherein Et is an ethyl group, Me is a methyl group and Cl is chloride.

The silane group, SN, allows the photoactivatable silane compounds to be covalently bound to the surface of a substrate such as silica. A linkage and spacer, LS, joins the silane to the photoactivatable group. The photoactivatable group, PG, forms a hydrophobic layer that can be photochemically cross-linked with a layer of hydrophilic polymers containing reactive functional groups. These functionalized polymers provide multiple points of attachment to the substrate and thus increase capacity for subsequent attachment of nucleic acid probes or other biopolymers, such as polypeptides and polysaccharides. This invention thus discloses a method to synthesize a substrate of hydrophobic layers and hydrophilic functionalized polymer layers thereafter onto glass surfaces.

Figure 1:
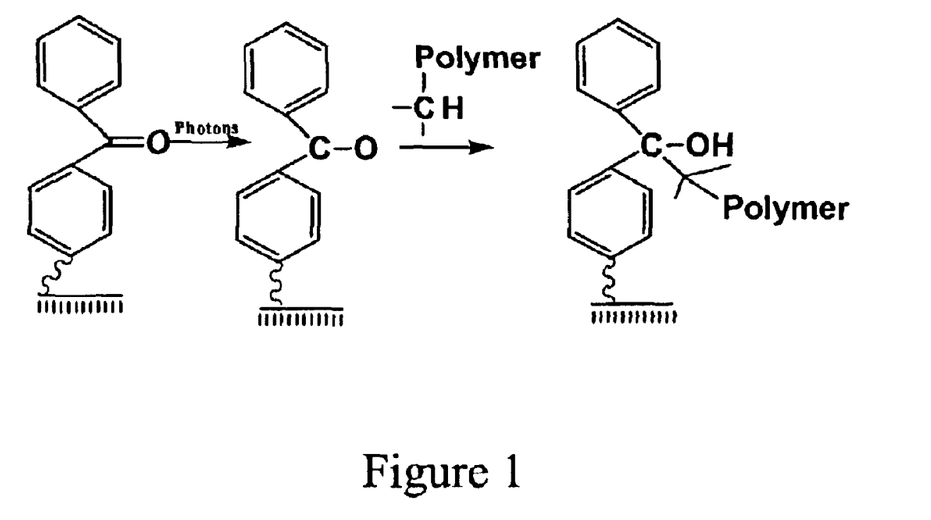
FIG. 1. Schematic diagram showing cross-linking of hydrophobic photoactivatable groups with hydrophilic polymers.

The hydrophobic photoactivatable group can cross-link photochemically to the hydrophilic polymers with a plurality of functional groups on the polymers as shown in FIG. 1.

Figure 2:
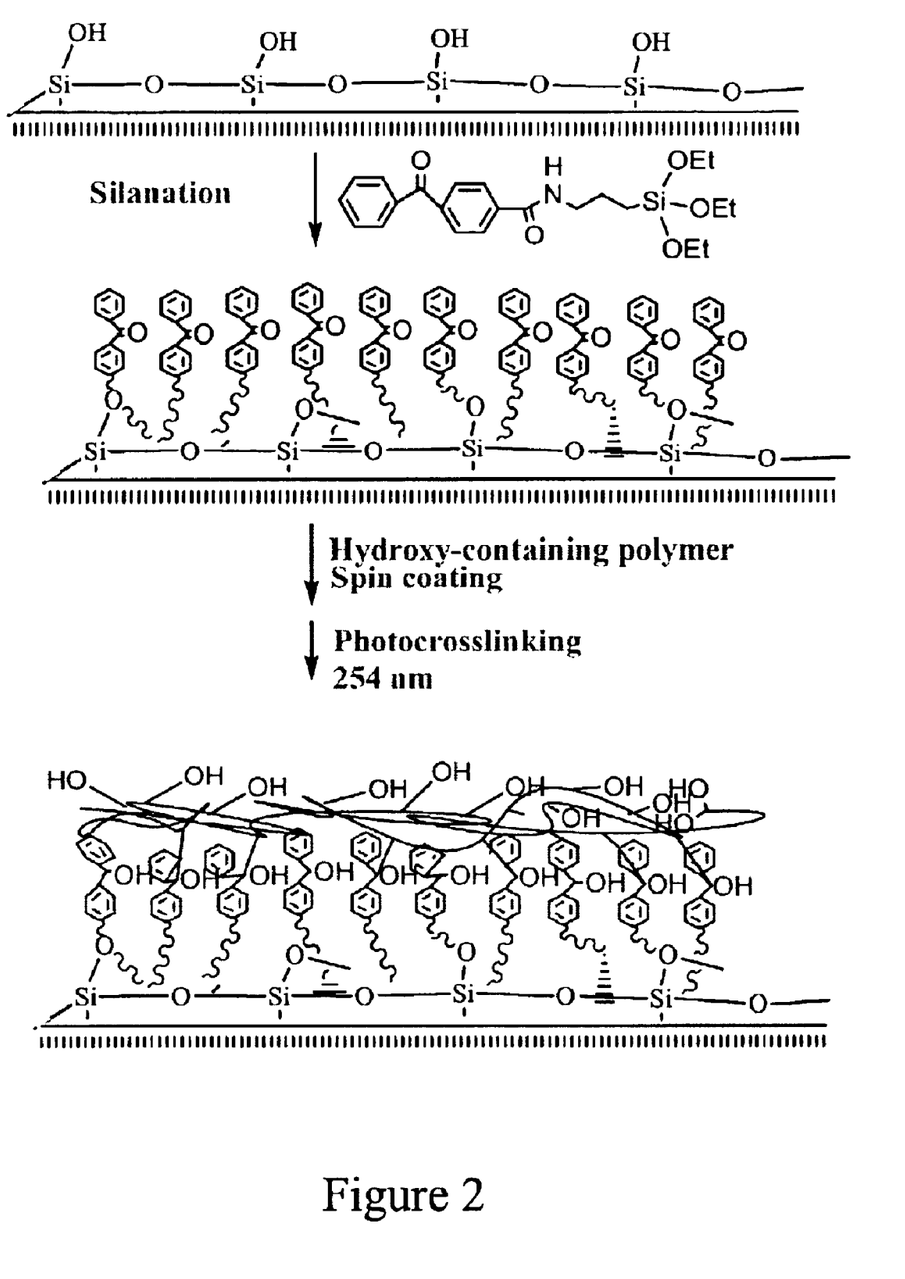
FIG. 2. Process of forming a functionalized surface: (i) silanation of photoactivatable silane compounds onto the surface of a substrate; (ii) photocrosslinking of the hydrophobic layer with hydrophilic polymers with hydroxyl groups.

Such cross-linking will thus form a multilayered polymer surface with reactive functional groups on the surface of a substrate such as silica as shown in FIG. 2.

Exemplary reactive functional groups include hydroxyl, amino, carboxyl and thiol, as well as modified forms thereof, such as activated or protected forms. The functionalized surfaces thus formed may be used in a wide range of different applications. In one embodiment, the functionalized surfaces are attached to the surface of a substrate comprising silica, such as a glass substrate, to which molecules, including polypeptides and nucleic acids, may be attached. In one preferred embodiment, after covalent attachment of a functionalized surface to the surface of a solid silica substrate to form a functionalized coating on the substrate, an array of nucleic acids may be covalently attached to the substrate. Therefore, the method permits the formation of high density arrays of nucleic acids immobilized on a substrate, which may be used in conducting high volume nucleic acid hybridization assays.

The polymer coated surfaces prepared by this method have many advantages. (1) An initial hydrophobic silane coating offers protection from unwanted hydrolysis, and thus increased coating stability. (2) Polymer grafting provides multiple points of attachment to the substrate, which further increases the stability of the coating. (3) A plurality of functional groups on the polymer provides increased capacity for subsequent attachment of nucleic acid probes or other biopolymers, compared to conventional silanated flat substrates. (4) The polymer composition can be controlled in order to optimize properties for a given application (porosity, functional group content, intermolecular spacing, etc.). (5) Photolithographic nucleic acid synthesis using MeNPOC chemistry results in substantially higher yield on these supports.

Photoactivatable group. The use of a photoactivatable group allows the hydrophobic photoactivatable groups to be photochemically cross-linked to the hydrophilic polymers with a plurality of functional groups on the polymers. Preferably, the photoactivatable groups will be cross-linked to the hydrophilic polymers by radiation in the ultraviolet (UV) or visible portion of the electromagnetic spectrum. More preferably, the photoactivatable groups will be irradiated in the near UV or visible portion of the spectrum. In some embodiments, however, activation may be performed by other methods such as localized heating, electron beam lithography, x-ray lithography, laser pumping, oxidation or reduction with microelectrodes, and the like. When light is used to activate various groups, the light may be from a conventional incandescent source, a laser, a laser diode, or the like. It may, further, be desirable in some embodiments to utilize groups which are sensitive to different wavelengths to control cross-linking.

Many, although not all, of the photoactivatable groups will be aromatic compounds that absorb near-UV and visible radiation. Suitable photoactivatable groups may be selected from a wide variety of positive light-reactive groups. Typical examples of photoactivatable groups are provided in Structure II described above.

Linkage and spacer group. A linkage and spacer group joins the photoactivatable group to the silane group of the photoactivatable silane compounds. A linkage and spacer group can be a bond or any structure that covalently join the photoactivatable group to the silane group of the photoactivatable silane compounds. The linkage and spacer group can be carbon—carbon single bonds, carbon—carbon double bonds, carbon-nitrogen single bonds, or carbon-oxygen single bonds. The length of linkage and spacer can be adjusted accordingly. Examples of suitable linkage and spacer groups are polyethyleneglycols, dicarboxylic acids, polyamines and alkylenes, substituted with, for example, methoxy and ethoxy groups. However, it is generally preferred that the linkage and spacer group includes a hydrocarbon chain, a —O—, —NH—CO—, —CO—NH—, or thiol linkage. Typical examples of a linkage and spacer group are provided in Structure III described above.

The Silane group. The term "silane" refers to a compound comprising a silicon atom. In a preferred embodiment, silane is a silylating agent comprising an activated silicon group, wherein the activated silicon group comprises a silicon atom covalently linked to at least one reactive group, such as an alkoxy or halide, such that the silicon group is capable of reacting with a functional group, for example on a surface of a substrate, to form a covalent bond with the surface. For example, the silane group on the photoactivatable silane compound can react with the surface of a silica substrate comprising surface Si—OH groups to create siloxane bonds between the silicon compound and the silica substrate.

Essentially, any conceivable substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoro-ethylene, (poly)vinylidenedifluoride, polystyrene, polycarbonate, or combinations thereof. Other substrate materials will be readily apparent to those of skill in the art upon review of this disclosure.

Typical examples of a silane group are provided in Structure IV described above. In a preferred embodiment, the photoactivatable silane compound is 4-(3'-triethoxysily)propylamidobenzophenone (APTSBP). In another preferred embodiment, the photoactivatable silane compound is 4-(3'-triethoxysilyl)propyloxybenzophenone.

Functionalized polymer. As used herein, the term "functionalized polymer" refers a hydrophilic polymer with reactive functional groups. The reactive functional groups can photochemically cross-link with a photoactivatable silane compound on a substrate such as silica. In a preferred embodiment, the functionalized polymer is a polymer containing hydroxyl groups. Other reactive functional groups include amino, carboxyl, thiol, and amide, as well as modified forms thereof, such as activated or protected forms. Reactive functional groups also include substitutable leaving groups such as halo or sulfonate. In one preferred embodiment, the reactive functional group is a group, such as a hydroxyl group, that is capable of reacting with activated nucleotides to permit nucleic acid synthesis.

For example, the functionalized polymer may be photochemically cross-linked to the photoactivatable silane compounds on the surface of a substrate, such as glass, and then reactive hydroxyl groups on the polymers may be reacted with an activated phosphate group on a protected nucleotide phosphoramidite or H-phosphonate, and then stepwise addition of further protected nucleotide phosphoramidites or H-phosphonates can result in the formation of a nucleic acid covalently attached to the support. The nucleic acids also may be attached to the reactive group via a linker. In a further embodiment, arrays of nucleic acids may be formed covalently attached to the substrate and are useful in conducting nucleic acid hybridization assays.

Typical examples of functionalized polymers are PVA (polyvinyl alcohol) and dextran. In a preferred embodiment, functionalized polymers include hydroxyl containing polymers such as hydroxyethycellulose, poly(2-hydroxylpropyl) methacrylate, 88% hydrolyzed PVA, 80% ethoxylated polyethylenimine, poly(vinylalcholo-co-ethylene), hydrogenated poly(phenyl vinyl ketone), reduced poly-glutaldehyde and dextran. In another preferred embodiment, functionalized polymers include polyacrylamide derivatives which can be homopolymer, random polymers and/or block polymers. Typical examples are Poly-HEAA (2-hydroxyethylacrylamide) and Poly-HEAA-MAA (2-hydroxyethylacrylamide-methylacrylamide).

Polynucleotides. The term "polynucleotide", "oligonucleotide", or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

For example, in one embodiment, the photoactivatable silane compounds cross-linked with functionalized polymers are used to form a coating on a solid substrate, and include functional groups that permit the covalent attachment or synthesis of nucleic acid arrays to the solid substrate, such as glass. The resulting substrates are useful in nucleic acid hybridization assays, which are conducted, for example in aqueous buffers. In one embodiment, preferred are photoactivatable silane compounds cross-linked with functionalized polymers that produce coatings that are substantially stable to hybridization assay conditions, such as phosphate or TRIS buffer at about pH 6–9, and at elevated temperatures, for example, about 25–65° C., for about 1 to 72 hours, such that hydrolysis is less than about 90%, e.g., less than about 50%, or e.g, less than about 20%, or about 10%. The surfaces on the substrate, formed by covalent attachment of photoactivatable silane compounds cross-linked with functionalized polymers, advantageously are substantially stable to provide a support for biopolymer array synthesis and to be used under rigorous assay conditions, such as nucleic acid hybridization assay conditions and polymerase chain reaction (PCR) conditions.

The surface in one embodiment includes at least one photoactivated silane compound group and at least one functionalized polymer group. In one embodiment, the surface includes at least one photoactivatable silane compound group and a plurality of functionalized polymer groups, for example, 2, 3, 4 or more functionalized polymer groups. In another embodiment, the surface includes at least one functionalized polymer group and a plurality of photoactivatable silane compound groups, for example, 2, 3, 4 or more photoactivatable silane compound groups. Methods of making the photoactivatable silane compounds are provided as disclosed herein. Methods of use of the photoactivatable silane compounds include covalent attachment of the photoactivatable silane compounds to substrate surface to form hydrophobic layers, and further photochemical cross-linking with hydrophilic functionalized polymer layers to provide a surface for arrays of nucleic acids.

Biopolymers. The term "biopolymer" as used herein refers to a polymeric form of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

For example, in one embodiment, the photoactivatable silane compounds cross-linked with functionalized polymers are used to form a coating on a solid substrate, and include functional groups that permit the covalent attachment or synthesis of biopolymer arrays to the solid substrate, such as glass.

In another embodiment, the functionalized polymers are reactive with activated oligonucleotides or peptides for the synthesis of oligonucleotides and peptides on the substrate. In yet another embodiment, the synthesizing of oligonucleotides and peptides on the functionalized polymer requires an activation of the functionalized polymers. In a further embodiment, an array of oligonucleotides or peptides is synthesized using photolithographic methods or other reagent deposition methods. Such reagent deposition methods may include inkjet methods as described in U.S. Pat. Nos. 5,831,070 and 6,239,273.

Applications. The methods and compositions disclosed herein may be used in a variety of applications. The photoactivatable silane compounds may be covalently attached to a variety of materials, and when cross-linked with functionalized polymers to provide reactive functional groups on the materials. For example, the material may comprise a silica material comprising surface silanols capable of reacting with the silane group to form a siloxane bond between the silicon atom on the photoactivatable silane compound and the silicon atom on the surface. Thus, the photoactivatable silane compounds may be attached to, for example, materials comprising silica, such as glass, chromatography material, and solid supports used for solid phase synthesis, such as nucleic acid synthesis. The photoactivatable silane compounds further may be attached to materials comprising oxides such as titanium(IV) dioxide and zirconium dioxide, aluminum oxide and indium-tin oxides, as well as nitrides, such as silicon nitride. Solid substrates which may be coated by the photoactivatable silane compounds include any of a variety of fixed organizational support matrices. Examples of substrates include slides, beads and solid chips.

The photoactivatable silane compounds used advantageously may be selected with selected properties for a particular application. Photoactivatable silane compounds may be selected which can form surface coatings that have good stability to hydrolysis. Photoactivatable silane compounds may be selected which have a selected reactivity with the substrate and a selected reactive functional group depending on the intended use.

In one embodiment, the photoactivatable silane compounds may be covalently attached to the surface of a solid substrate to provide a coating comprising hydrophobic layers on the substrate, and upon cross-linking with hydrophilic reactive polymer layers, thus permitting arrays of immobilized oligomers to be covalently attached to the substrate via covalent reaction with the reactive functional groups. The immobilized oligomers, such as polypeptides, or nucleic acids can be used in a variety of binding assays including biological binding assays. In one embodiment, high density arrays of immobilized nucleic acid probes may be formed on the substrate, and then one or more target nucleic acids comprising different target sequences may be screened for binding to the high density array of nucleic acid probes comprising a diversity of different potentially complementary probe sequences. For example, methods for light-directed synthesis of DNA arrays on glass substrates is described in McGall et al., *J. Am. Chem. Soc.*, 119:5081–5090 (1997), the disclosure of which is incorporated herein.

Methods for screening target molecules for specific binding to arrays of polymers, such as nucleic acids, immobilized on a solid substrate, are disclosed, for example, in U.S. Pat. No. 5,510,270, the disclosure of which is incorporated herein. The fabrication of arrays of polymers, such as nucleic acids, on a solid substrate, and methods of use of the arrays in different assays, are also described in: U.S. Pat. Nos. 5,744,101, 5,677,195, 5,624,711, 5,599,695, 5,445,934, 5,451,683, 5,424,186, 5,412,087, 5,405,783, 5,384,261, 5,252,743 and 5,143,854; and PCT WO 92/10092, the disclosures of each of which are incorporated herein. Accessing genetic information using high density DNA arrays is further described in Chee, *Science* 274:610–614 (1996), the disclosure of which is incorporated herein by reference. The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS®) arrays, as described in U.S. Pat. No. 5,631,734, the disclosure of which is incorporated herein.

In the embodiment wherein solid phase chemistry, photolabile protecting groups and photolithography are used to create light directed spatially addressable parallel chemical synthesis of a large array of polynucleotides on the substrate, as described in U.S. Pat. No. 5,527,681, the disclosure of which is incorporated herein, computer tools may be used for forming arrays. For example, a computer system may be used to select nucleic acid or other polymer probes on the substrate, and design the layout of the array as described in U.S. Pat. No. 5,571,639, the disclosure of which is incorporated herein.

Substrates having a surface to which arrays of polynucleotides are attached are referred to herein as "biological chips". The substrate may be, for example, silicon or glass, and can have the thickness of a microscope slide or glass cover slip. Substrates that are transparent to light are useful when the assay involves optical detection, as described, e.g., in U.S. Pat. No. 5,545,531, the disclosure of which is incorporated herein. Other substrates include Langmuir Blodgett film, germanium, (poly)tetrafluorethylene, polystyrene, (poly)vinylidenedifluoride, polycarbonate, gallium arsenide, gallium phosphide, silicon oxide, silicon nitride, and combinations thereof. In one embodiment, the substrate is a flat glass or single crystal silicon surface with relief features less than about 10 Angstroms.

The surfaces on the solid substrates will usually, but not always, be composed of the same material as the substrate. Thus, the surface may comprise any number of materials, including polymers, plastics, resins, polysaccharides, silica or silica based materials, carbon, metals, inorganic glasses, membranes, or any of the above-listed substrate materials. Preferably, the surface will contain reactive groups, such as carboxyl, amino, and hydroxyl. In one embodiment, the surface is optically transparent and will have surface Si—OH functionalities such as are found on silica surfaces.

In the embodiment wherein arrays of nucleic acids are immobilized on a surface, the number of nucleic acid sequences may be selected for different applications, and may be, for example, about 100 or more, or, e.g., in some embodiments, more than $10^5$ or $10^8$. In one embodiment, the surface comprises at least 100 probe nucleic acids each preferably having a different sequence, each probe contained in an area of less than about 0.1 cm$^2$, or, for example, between about 1 $\mu$m$^2$ and 10,000 $\mu$m$^2$, and each probe nucleic acid having a defined sequence and location on the surface. In one embodiment, at least 1,000 different nucleic acids are provided on the surface, wherein each nucleic acid is contained within an area less than about $10^{-3}$ cm$^2$, as described, for example, in U.S. Pat. No. 5,510,270, the disclosure of which is incorporated herein.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different nucleic acids is greater than about 60 different nucleic acids per 1 cm$^2$.

Arrays of nucleic acids immobilized on a surface which may be used also are described in detail in U.S. Pat. No. 5,744,305, the disclosure of which is incorporated herein. As disclosed therein, on a substrate, nucleic acids with different sequences are immobilized each in a predefined area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 cm$^2$ to $10^{-10}$ cm$^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, $10^{-10}$ cm$^2$. For example, in one embodiment, there is provided a planar, non-porous support having at least a first surface, and a plurality of different nucleic acids attached to the first surface at a density exceeding about 400 different nucleic acids/cm$^2$, wherein each of the different nucleic acids is attached to the surface of the solid support in a different predefined region, has a different determinable sequence, and is, for example, at least 4 nucleotides in length. The nucleic acids may be, for example, about 4 to 20 nucleotides in length. The number of different nucleic acids may be, for example, 1000 or more. In the embodiment where polynucleotides of a known chemical sequence are synthesized at known locations on a substrate, and binding of a complementary nucleotide is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270, the disclosure of which is incorporated herein.

Devices for concurrently processing multiple biological chip assays may be used as described in U.S. Pat. No. 5,545,531, the disclosure of which is incorporated herein. Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832, the disclosure of which is incorporated herein. These methods permit a highly sensitive and resolved image to be obtained at high speed. Methods and apparatus for detection of fluorescently labeled materials are further described in U.S. Pat. Nos. 5,631,734 and 5,324,633, the disclosures of which are incorporated herein.

The methods and compositions described herein may be used in a range of applications including biomedical and genetic research and clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839, the disclosure of which is incorporated herein. The nucleic acid arrays may be used in many other applications including detection of genetic diseases such as cystic fibrosis, diabetes, and acquired diseases such as cancer, as disclosed in U.S. Pat. Nos. 5,837,832, 5,861,242, 6,027,880, the disclosure of which is incorporated herein. Genetic mutations may be detected by sequencing by hybridization. In one embodiment, genetic markers may be sequenced and mapped using Type-IIs restriction endonucleases as disclosed in U.S. Pat. No. 5,710,000, the disclosure of which is incorporated herein.

Other applications include chip based genotyping, species identification and phenotypic characterization, as described in U.S. Pat. No. 6,228,575, and U.S. application Ser. No. 08/629,031, filed Apr. 8, 1996, the disclosures of which are incorporated herein.

Gene expression may be monitored by hybridization of large numbers of mRNAs in parallel using high density arrays of nucleic acids in cells, such as in microorganisms such as yeast, as described in Lockhart et al., *Nature Biotechnology,* 14:1675–1680 (1996), the disclosure of which is incorporated herein. Bacterial transcript imaging by hybridization of total RNA to nucleic acid arrays may be conducted as described in Saizieu et al., *Nature Biotechnology,* 16:45–48 (1998), the disclosure of which is incorporated herein.

Other applications include PCR (polymerase Chain Reaction) on chips. The substrates prepared by the photoactivatable silane compounds in this invention are stable under conditions for polymerase chain reactions, and therefore allow one of skill in the art to carry out manipulations such as polymerase chain reactions and other reactions on a chip.

The invention will be further understood by the following non-limiting examples.

EXAMPLES

Example 1

Photoactivatable silane compounds are synthesized and bound to the surface of a substrate such as silica. Hydrophilic polymers with reactive functional groups (hydroxyl-containing polymer) are applied to the substrate, and then photochemically cross-linked to the hydrophobic layers to form a surface with a plurality of functional groups on the polymer. FIG. 2 shows a schematic diagram of such a process.

Example 2

Figure 3:
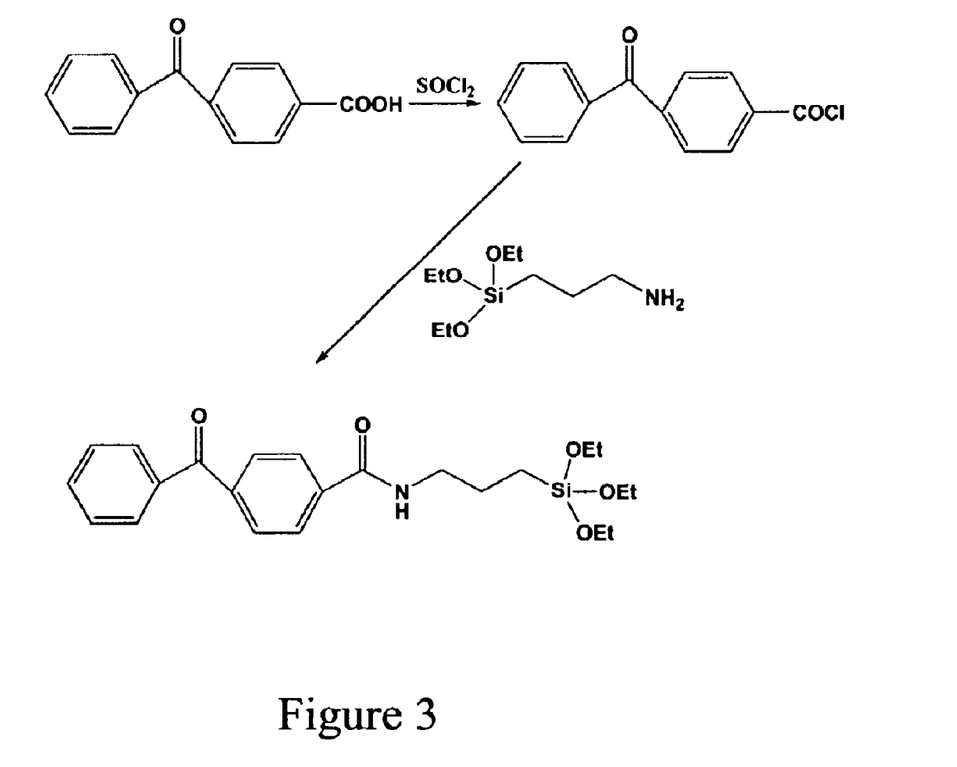
FIG. 3. Synthesis of 4-(3'-triethoxysily) propylamidobenzophenone (APTSBP) using benzoybenzoic acid chloride and amniopropyltriethoxysilane.

Synthesis of 4-(3'-triethoxysily) propylamidobenzophenone (APTSBP) Using Benzoybenzoic acid Chloride and amniopropyltriethoxysilane FIG. 3 shows a reaction demonstrating the synthesis of 4-(3'-triethoxysily)propylamidobenzophenone (APTSBP) using benzoybenzoic acid chloride and amniopropyltriethoxysilane.

Procedures:

$SOCl_2$ (50 ml) was introduced into a three neck round bottom flask equipped with a condenser, drying tube and a gas bubbler under Ar. Benzoybenzoic acid (BP—COOH) (13.8 g) was added to the flask. The BP—COOH was not soluble. The mixture was stirred for half hour at room temperature and then slowly heat to reflux. Control the heating and watch for gas release. The BP—COOH was totally dissolved after 20 minutes of reflux. No more gas was generating after 40 minutes, indicating the reaction was complete. The mixture was stirred for one more hour after no more gas is generating. The excess $SOCl_2$ was removed by distillation most first. The minor left over was thoroughly removed under vacuum. Use two dry ice cold trap and NaOH solid trap to avoid damage to the pump. An oiless, Teflon paraphram pump would be recommended for this usage. A light yellowish solid was obtained. 14.6 g. Run GC-MS to characterize.

Synthesis of APTSBP:

Aminopropyltriethoxysilane (FW=221.37, d=0.946, 13.2 g, 14 ml, 0.06 moles), triethylamine (TEA, FW=101, d=0.73, 6.06 g, 8.3 ml, 0.06 moles), and anhydrous tetrahydrofuran (THF, 20 ml) were introduced into a three neck round bottom flask under Ar. The mixture was cooled in an ice bath. BPCOCl (14.6 g, FW=244.5, 0.06 moles) dissolved in 50 ml of anhydrous THF was added drop wise with good stirring. Fume of $Et_3N$—HCl could be observed. White precipitate formed after 10 ml was added. The ice bath was removed after addition. The final mixture was further stirred for one hour, at the time the mixture was warmed up to room temperature. Prepare filtration equipment in glove box under dry nitrogen. The solid was filtered off. Wash with dry THF (10 ml). The filtrate was passed through silica gel (30 g, in a Buchner funnel) under vacuum. Wash the silica with THF (10 mL). The final filtrate was put on a rotavap to remove THF. A light yellowish solid was obtained and dried under vacuum. Run NMR and GC_MS to characterize. The process has a yield of 24 g at 92%.

Example 3

Synthesis of 4-(3'-triethoxysilyl) propyloxybenzophenone Using a Homogeneous Pt.

Figure 4:
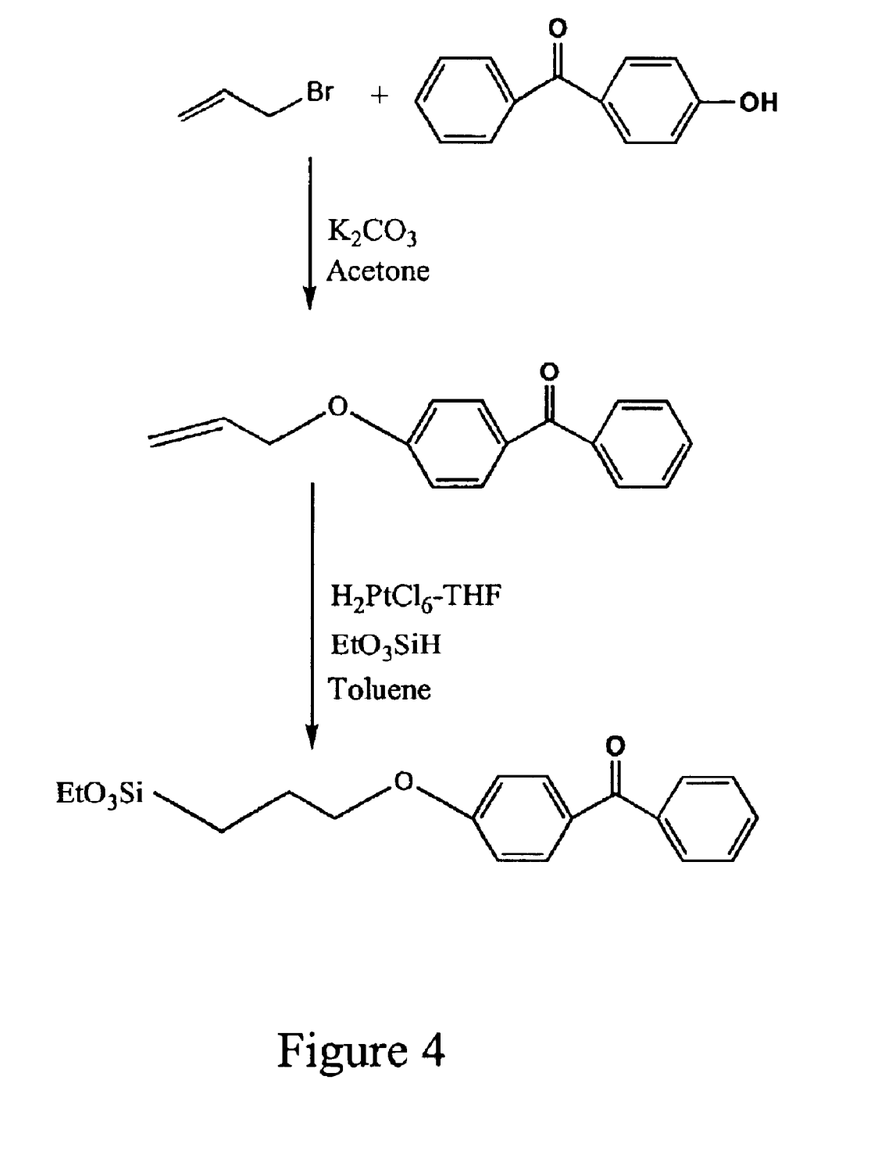
FIG. 4. Synthesis of 4-(3'-triethoxysilyl) propyloxybenzophenone using a homogeneous Pt.

FIG. 4 shows a reaction demonstrating the synthesis of 4-(3'-triethoxysilyl)propyloxybenzophenone using a homogeneous Pt.

Preparation of Catalyst:

Hydrogen hexachloroplatinate hydrate (250 mg) was dissolved in 10 ml anhydrous THF. A turbid solution was obtained. Add 2 g of anhydrous $NaSO_4$. The resulting clear solution was used as the catalyst stock solution, assuming a concentration of 20 mg/ml. This catalyst can be stored in dark and dry environment and stay good for at least a week.

Preparation of Charcoal-Silica Column:

Use a cork borer to cut filter paper with a size to fit the inside of the syringe. Push two pieces to the bottom and press tightly. Load silica gel and charcoal with care.

Hydrosilation:

4-allyloxybenzophenone (FW=238, 0.084 mole, 20 g), dissolved in 200 ml dry toluene, and 1.0 ml of catalyst stock was added into a three neck round bottom flask with stirring under argon or nitrogen. The solution may appear cloudy, but will become clear after heating. Triethoxysilane (FW=164, 0.084 molex3, 41 g, 46.5 ml) was added drop wise to the flask under argon. One neck was equipped with a thermometer. No temperature change was observed during addition. The mixture was first stirred at room temperature for 2 hours. Then, the mixture was heated up and stirred at 50° C. for 24 hours. Take 2.0 ml reaction mixture out. Filter through a 3 ml syringe packed with 0.2 ml of charcoal and 0.2 ml of silica under nitrogen in a glove box. Remove the solvent and excess triethoxysilane under vacuum. Run NMR to identify the products and monitor the completion of the reaction. The reaction is complete after 24 hours. Prepare silica gel-charcoal pad. Use a fritted glass Buchner funnel, place a filter paper, load 10 g silica gel and then 5 g of charcoal, with care. Filter the reaction mixture through charcoal-silica gel into a round bottom flask under argon in a glove box. Apply vacuum on filtration. Make sure the charcoal-silica gel is packed tightly. Test with some anhydrous toluene first before reaction mixture is loaded. Prepare the rotavap. Remove all toluene and most of the excess $EtO_3SiH$ under vacuum. The $EtO_3SiH$ is hard to get rid of. Add back some anhydrous toluene and do rotavap repeatedly. This will help remove any residual of $EtO_3SiH$. Rotating the flask will also help. Check NMR or weigh to detect the complete deletion of starting material $EtO_3SiH$. The yield is quantitative. The identity is confirmed by $^1HNMR$, $^{13}CNMR$, UV-Vis, GC-MS, and FT-IR.

Example 4

Figure 5:
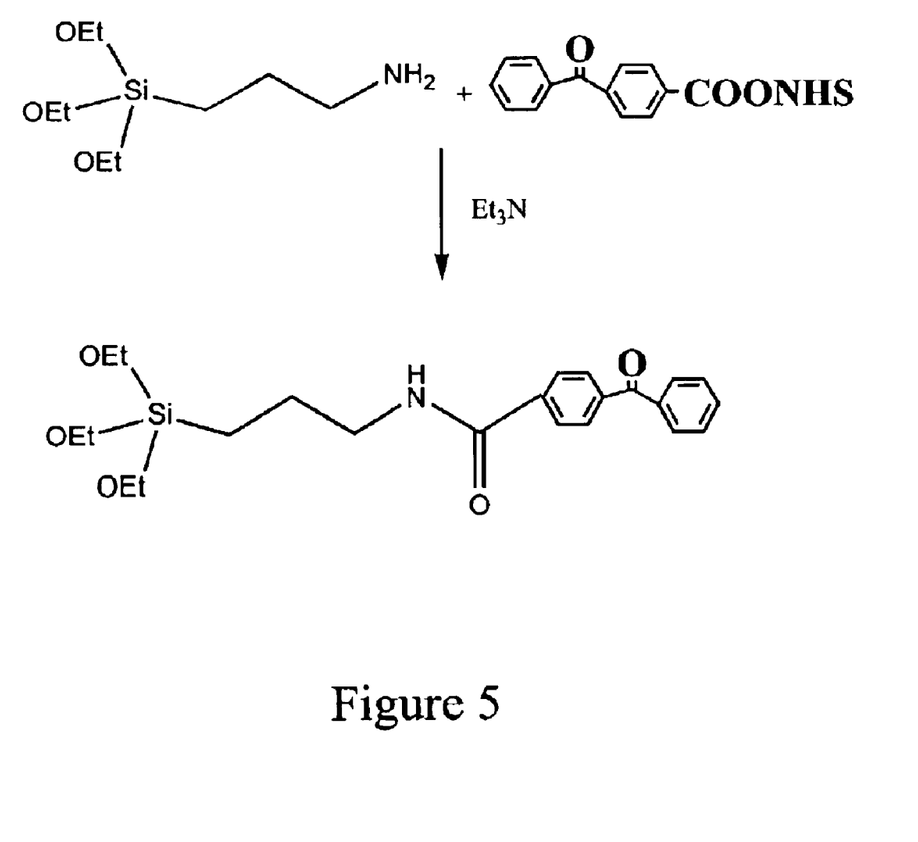
FIG. 5. Synthesis of 4-(3'-triethoxysily) propylamidobenzophenone (APTSBP) using benzoybenzoic acid NHS ester and amniopropyltriethoxysilane.

Preparation of triethoxylbenzoybenzamidopropylsilane and silanation on Glass Slides FIG. 5 shows a schematic reaction to make a benzophenone glass surface.

Materials and Equipment:

3-aminopropyltrimethoxylsilane (APTS) (d=0.95, FW=221.4), Benzoylbenzoic acid NHS ester (BPNHS) (B4412, FW-=323), Triethylamine (TEA, d=0.73, FW=101.2), Anhydrous cyclohexane, Anhydrous DMF, and iso-propyl alcohol (IPA).

Procedures:

APTS (0.1 ml, 0.43 mmoles) is dissolved in 0.1 ml dry DMF.Add TEA (0.43×1.2→0.52 mmoles, 72 µl). Add BPNHS solution (0.43×2→0.86 mmoles, 0.25 g in 2 ml dry DMF. Stir for 1.0 hour. Load 0.5 mL reaction mixture onto each glass slide (Soda Lime) and incubate at room temperature for 15 minutes. Rinse the slide with DMF, and acetone and iso-propanol. Silanation went well by checking the wetability.

Example 5

Photo Attachment of Polymers onto BP Glass Surface

| Materials Polymer | Concentration |
| --- | --- |
| PVA, 31–50 K, 88% hydrolyzed | water, 25% |
| PVA, 13–23 K, 88% hydrolyzed | water, 25% |
| dextran, 37.5 K | water, 40% |
| dextran, 2 M | water, 40% |

Procedures:

Make polymer solution a day before coating. Load 1 ml of polymer solution on each slide, make sure the center area is covered big enough for later on oligonucleotide synthesis. For the polymer in organic solution, load 1 ml and allow the slides dry in a hood. Irradiate under 254 nm, for 15 minutes in BioLink UV box. Total energy=2.2 joules. Remove the polymer from slides and rinse with water. Sonicate the slides for 1 minute. Soak the slide overnight in water. For organic soluble polymer, rinse with compatible solvent and soaked in the same solvent. Rinse with iso-propanol and dry with $N_2$ gun. Store slides in a desiccator. The slides are ready for oligonucleotide synthesis.

Example 6

Substrate Stability by Fluoroprime Assay

This experiment compares the stability of a substrate prepared by a photoactivatable silane compound and PVA as described in Example 5 above to a substrate prepared from a simple silane.

Figure 6:
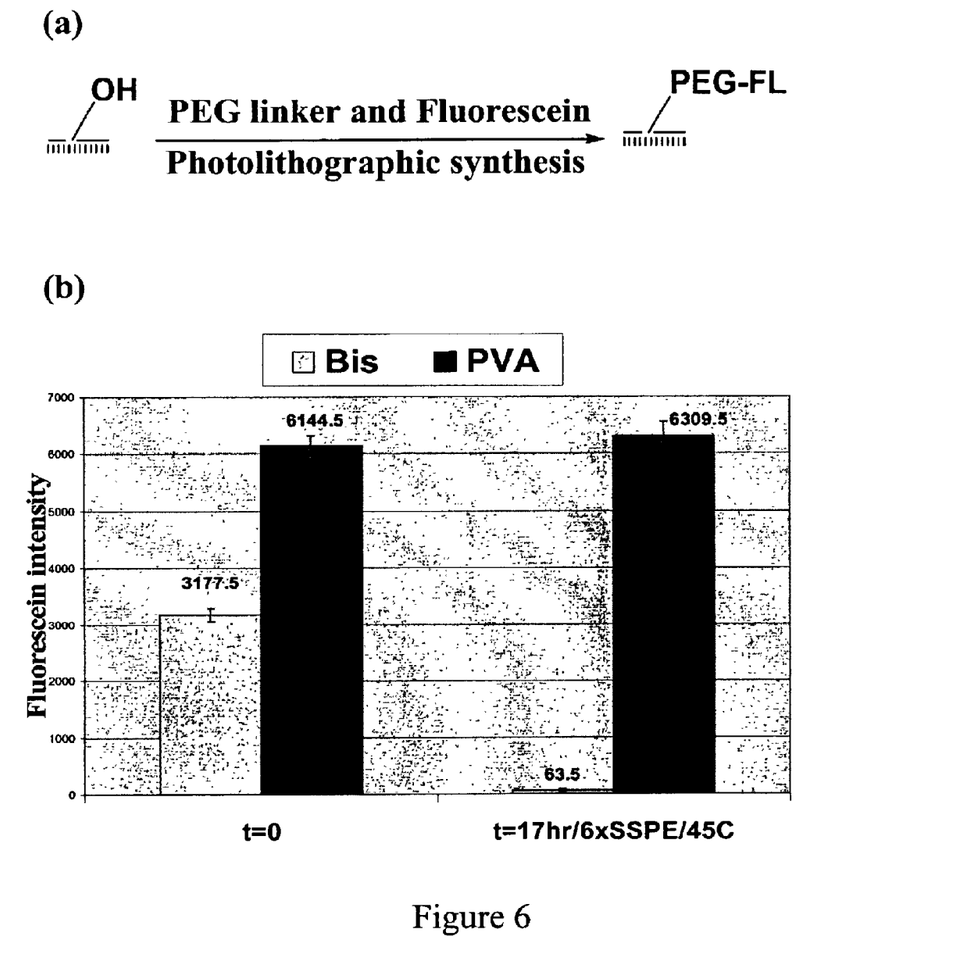
FIG. 6. Diagram showing stability of substrate prepared with APTSBP and PVA.

A substrate slide was mounted onto a flow cell connected with an ABI synthesizer, following a standard synthesis cycle as described in McGall et al, J. Am. Chem. Soc., 119:5081–5090 (1997). First the MeNPOC polyethyleneglycol phosphoramidite was coupled on the substrate and capped with dimethyl-N,N-diisopropylphosphoramidite. The substrate was washed with acetonitrile and dried with Ar. A strip patterned mask was used to mask the substrate and a 365 nm light source was applied (total 6 Joules) for the photolysis. A mixture of fluorescein phosphoramidite (0.5 mM) and DMT-dT phosphoramidite (49.5 mM) was introduced to react with the hydroxyls released from photolysis. The fluorescein was deprotected by ethylenediamine:ethanol (1:1) at room temperature for one hour. The substrate was then scanned for fluorescence signal on a scanner. To test the stability of the substrate, the scanned slides were soaked in a 0.1 M Sodium phosphate, 0.5 sodium chloride, 0.01% Triton, pH 7.8 buffer for 20 hours at 45 degree C. The slides were rinsed with water and re-scanned. The Experiment design is also shown in FIG. 6(a). The substrate prepared by the photoactivatable silane compounds are more stable than simple silane treated substrate, as shown in FIG. 6(b).

Example 7

T 6mer Synthesis on PVA Slides and Bis Silane Slides

The following example evaluates oligonucleotide probe synthesis on PVA substrate as prepared in Example 5.

An oligonucleotide dT 6mer (dTTTTTT) was synthesized on an ABI synthesizer using standard DNA synthesis cycles as described in McGall et al., J. Am. Chem. Soc., 119:5081–5090 (1997). Photodeprotection was performed with an open square mask using 6 joules of 365 nm irradiation. The sequence of coupling is the following: A spacer, the MeNPOC polyethyleneglycol phosphoramidite; Unreacted hydroxyls capping, dimethyl-N,N-diisopropylphosphoramidite; A cleavable linker, 2-[2-(4,4'-dimethoxyltrityloxy)ethylsulfony]ethyl-(2-cyanoethyl)-(N,N-diisopropyl)phosphoramidite; A fluorescent label, 5-carboxyfluorescein phosphoramidite; and then 6mer of dT, 5'-MeNPOC dT phosphoramidite. After synthesis, the dT 6mer was cleaved into 1.0 ml of ethylenediamine:water(1:1) at 50 degree C. for 4 hours. The cleaved oligonucleotides were analyzed by HPLC using fluorescence detector. The result provided a 60% increase in the amount of DNA synthesized per unit area of substrate.

Example 8

Preparation of Benzobenzoyl Aminopropyltriethoxysilane and Silanation in Toluene Procedures:

Benzobenzoic acid (FW=226.2, 3.3 g) is dissolved in 36 mL dry DMF. Add TEA (2.6 mL). DSC (FW=256, 5 g) was added in several portions. Solid DSC was dissolved in first one or two minutes resulting a clear solution. A solid (product) crashed out after 5 minutes. The mixture was stirred for total 20 minutes. 3-aminopropyltrimethoxylsilane (APTS) (d=0.95, FW=221.4) (3.4 ml) was added drop wise to the mixture with vigorous stirring. The solid is dissolving resulting in a clear solution in one minute. The clear solution was stirred for one more hour and added to 600 ml anhydrous toluene, ready for silanation. The clean sodalime slides were soaked in toluene for 15 minutes before they were transferred into silane tank. The silanation was incubated for two hours at room temperature with mild agitation. The slides were then washed with toluene (5 minutes×2) and isopropanol (5 minutes×1) and dried in an oven for 5 minutes at 50 degree C.

Example 9

Co-polymerization of N,N-dimethylacrylamide (DMA), Acrylamide and N-(2-hydroxypropyl) methacrylamide (HPMA)

Procedures:

An aqueous solution of acrylamides is placed in a glass reactor at room temperature. Four reactors were connected in a line. Nitrogen is passed over or bubbled through the solution during the experiment to diminish the amount of dissolved oxygen in the solution. A potassium persulfate solution was then added after 30 minutes of initial nitrogen bubbling. The polymerization was continued for 7 hours.

Stock solutions:

50% Acrylamide: 50 g, add 50 ml water, heat to dissolve in a water bath (30° C.).

20% DMA: 20 g, add 80 ml water

20% HPMA: 20 g, add 80 ml water.

10% Ammonium persulfate: 1 g, add water to 10 ml.

TABLE 1

(stock solution volume in parathesis)

| # | Mol %, DMA | Mol %, HPMA | Mol % Persulfate | Temperature | Time (hour) |
|---|---|---|---|---|---|
| A | 0 | 100 (30 ml) | 0.2 (0.22 ml) | 25° C. | 7 |
| B | 81.1 (22.5 ml) | 18.7 (7.5 ml) | 0.2 (0.22 ml) | 25° C. | 7 |
| C | 0 | 100 (30 ml) | 0.1 (0.11 ml) | 25° C. | 7 |
| D | 81.1 (22.5 ml) | 18.7 (7.5 ml) | 0.1 (0.11 ml) | 25° C. | 7 |

TABLE 2

| # | % Acrylamide | % HPMA | % Persulfate | Temperature | Time (hr) |
|---|---|---|---|---|---|
| E | 85.6 (9 ml stock) (13.5 ml H$_2$O) | 14.2 (7.5 ml) | 0.2 (0.22 ml) | 25° C. | 14 |
| F | 94 (22.5 ml) | 5.8 (7.5 ml) | 0.2 (0.22 ml) | 25° C. | 14 |

The solution became viscous after polymerization. A, C and E are more viscous, B and D are less viscous. F became a gel. The MW determination was not performed. Puddle coat benzophenone slides with the polymer solution. Irradiate under 254 nm for 10 minutes. Sonicate for 1 minute and soak in pure water overnight. Wash with water three times and iso-propanol one time and dry with nitrogen gun and ready for evaluation by FluoroPrime.

Example 10

Synthesis of Poly-HEAA (2-hydroxyethylacrylamide) and Poly-HEAA-MAA (2-hydroxyethylacrylamide-methylacrylamide)

Figure 7:
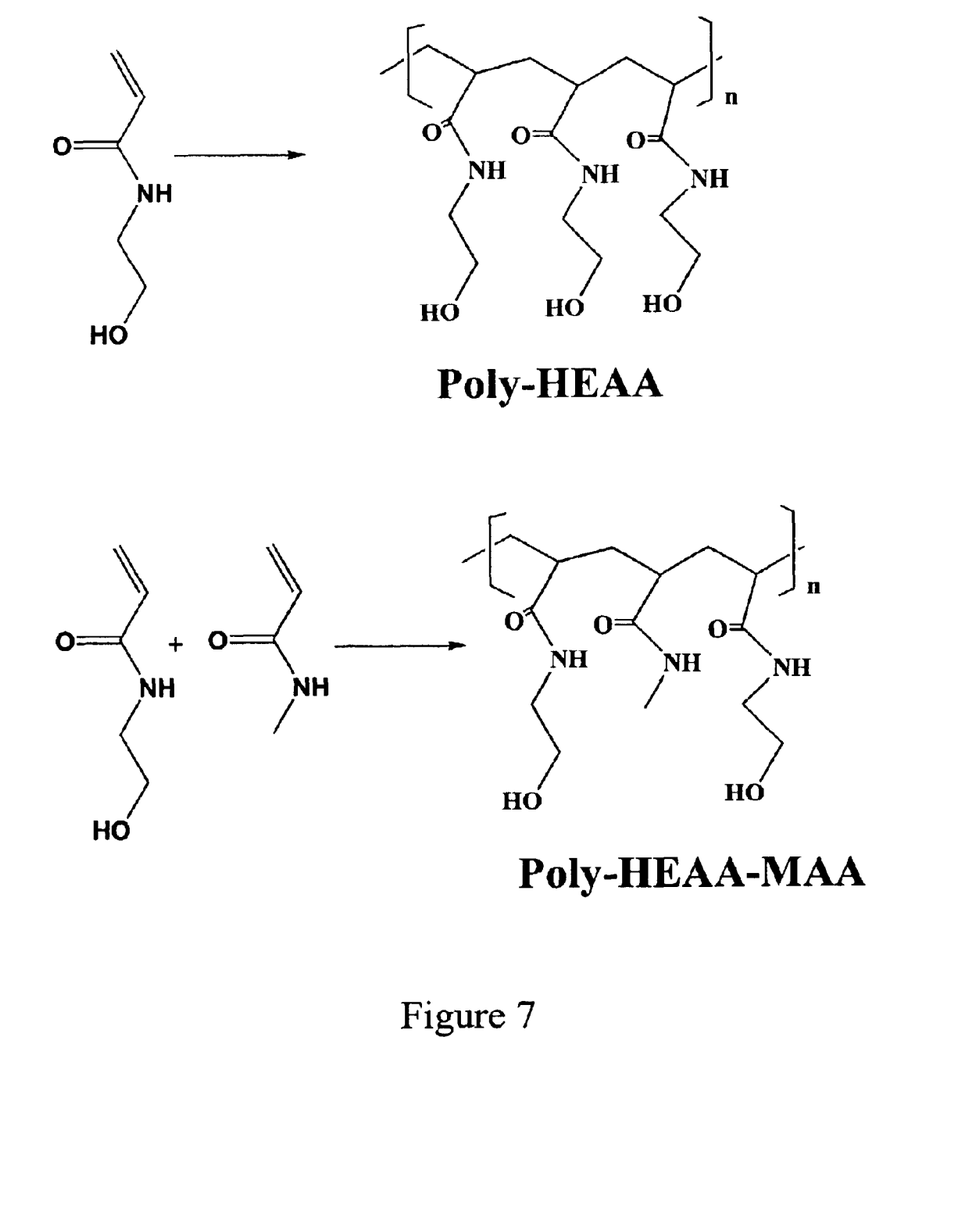
FIG. 7. Synthesis of Poly-HEAA (2-hydroxyethylacrylamide) and Poly-HEAA-MAA (2-hydroxyethylacrylamide-methylacrylamide).

Reactions for synthesis of poly hydroxyethyl acrylamide (poly-HEAA) and Poly-HEAA-MAA are shown in FIG. 7. Specifically, the synthesis of poly hydroxyethyl acrylamide (poly-HEAA) is described as follows. Poly methyl acrylate (50% stock in toluene, 20 ml), hydroxyethylamine (20 ml) were introduced in a flask. DMF (25 ml) was added to enhance solubility and a clear solution was obtained. Heat to reflux for 3 hours. Remove the solvent under vacuum. The residual was dissolved in 150 ml cold water and dialyzed against mill Q water in a dialysis tube with a molecular weight cut off of 10 KDa. The final was reconstituted into one liter water solution. It is 1% poly HEAA.

Figure 8:
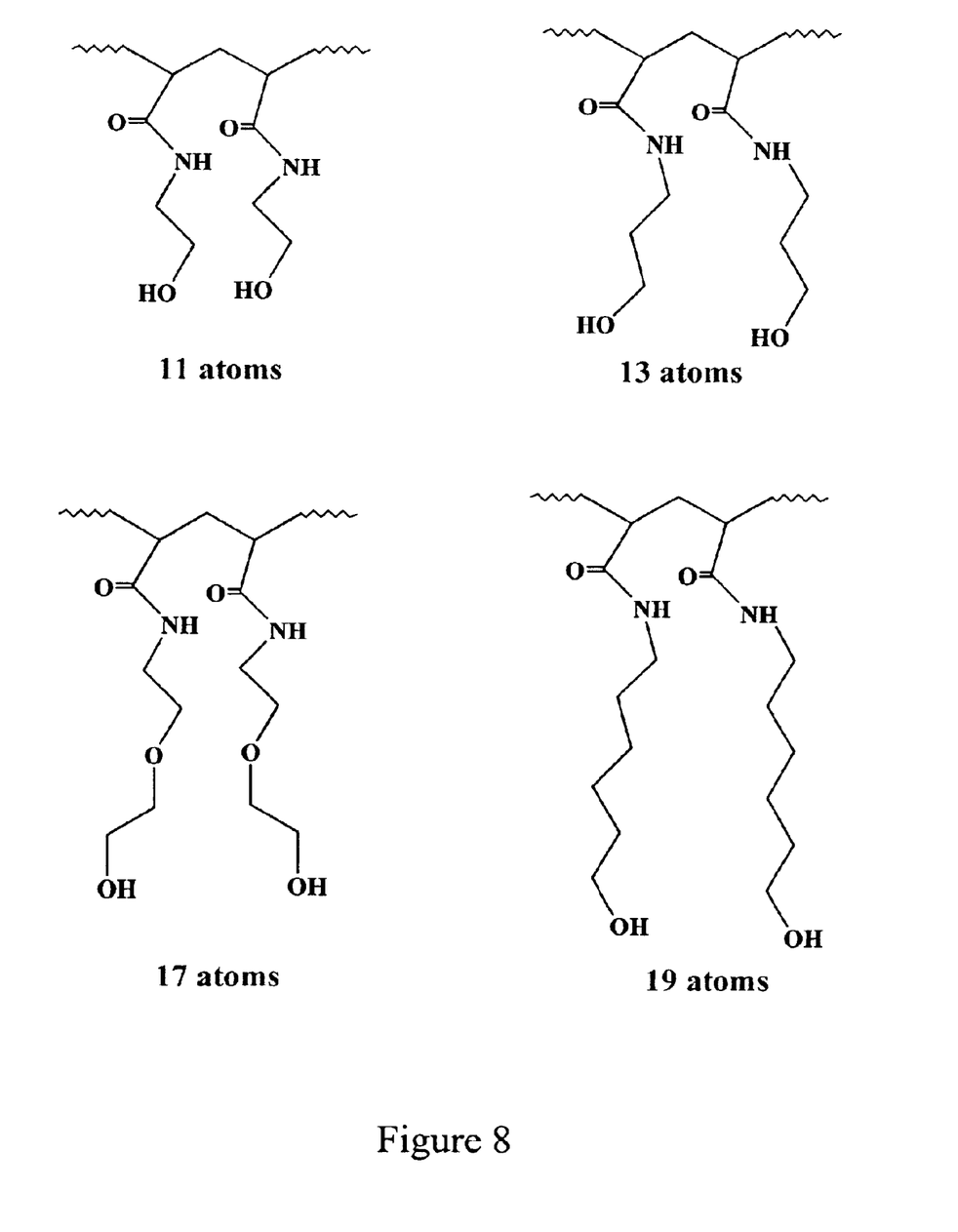
FIG. 8. Structure of hydroxyl-containing polymers with different linkage and spacer groups.

Examples of several synthesized hydroxyl containing polymers with different linkage and spacer groups are shown in FIG. 8.

Example 11

Preparation of Poly HEAA Surface Using Spin Coating Benzophenone Slides and Photocrosslinking.

Load 1 ml of poly HEAA per benzophenone slide (see example 4). Spin at 2K rpm for 20 seconds. Dry the slides in an oven at 50° C. for 30 minutes. Replace the slides under UV light (254 nm) for 20 minutes. The slides were sonicated for 5 minutes, soaked in water overnight, dried with blowing nitrogen and in an oven at 50° C. for 5 minute.

Example 12

Preparation of Poly Aldehyde Surface from Dextran Surface

Make a fresh sodium periodate solution (0.1 M) in mili Q water. Place dextran coated substrates (see example 5) in the solution. Incubate for 1.0 hour at room temperature.

Thoroughly rinse the substrate with water and then dried with blowing nitrogen. The poly aldehyde substrate was stored under dark. It was ready for immobilization of amino derivatized oligos.

Example 13

Oligonucleotide Spotting Procedure

Amino derivatized oligonucleotides were spotted on the aldehyde slides prepared in Example 12. Two-fold serially diluted solutions from 50 μM to 0.31 μM of two amino derivatized oligonucleotides of 25 mers and 50 mers were prepared. Twenty μl of each concentration were spotted in 8 replicate spots in a spotting buffer (3×SSC and 0.1% Sarcosine). After spotting, slides were baked at 80° C. for 20 min. and then treated with Sodium Borohydride for 5 min in 20 mM $NaBH_4$ in PBS and 23% Ethanol. Slides were rinsed with 0.2% SDS for 1 minute and then rinsed with water for 1 minute.

Targets are complementary oligonulceotides labeled with fluorescent dye Cy3. Slides were hybridized with targets in hybridization buffer (2×SSC, 0.1% SDS and complementary target at 100 nM) at room temperature for 1 hr and washed in 2×SSC, 0.1% SDS for 5 min., 0.1×SSC, 0.1% SDS for 10 min., and finally in 0.1×SSC for 1 min. All washings were carried out at room temperature. Results show that the aldehyde slides prepared from photoactivatable silane gave much higher hybridization signal than non-aldehyde slides.

Example 14

Stability of Oligonucleotides on the Substrate Under PCR Conditions

A 25-mer amino derivatized oligonucleotide was spotted and treated on the substrate as described in Example 13. The slides were scanned for the fluorescence signal before and after the slides were incubated in a typical PCR buffer (2.5 mM MgCl, 10 mM Tris-HCl, 50 mM KCl, pH 8.0). The result indicated that the oligonucleotides prepared on the substrate with photoactivatable silane compounds are more stable than oligonucleotides prepared on the substrate with aldehyde silane (CEL Associate, Houston, Tex.).

What is claimed is:

1. A photoactivatable silane compound of the formula PG-LS-SN wherein PG is a photoactivatable group for photochemically crosslinking, LS is a linkage and spacer group and SN is a silane group.

2. A photoactivatable silane compound according to claim 1 wherein said photoactivatable group for photochemically crosslinking is selected from a group consisting of the following moieties:

3. A photoactivatable silane compound according to claim 1 wherein said photoactivatable group for photochemically crosslinking comprises a photoreactive benzophenone.

4. A photoactivatable silane compound according to claim 1 wherein said saline group comprises an activated silicon group.

5. A photoactivatable silane compound according to claim 1 wherein said activated silicon group is capable of reacting with a functional group on a surface of a substrate.

6. A photoactivatable silane compound according to claim 4 wherein said saline group is selected from a group consisting of 7. A photoactivatable silane compound according to claim 1 wherein said photoactivatable silane compound is 4-(3'-triethoxysily)propylamidobenzophenone or 4-(3'-triethoxysilyl)propyloxybenzophenone.

8. A photoactivatable silane compound according to claim 1 wherein said LS group is selected from the group consisting of and 9. An array of biopolymers comprising:
a substrate,
a photoactivatable silane compound covalently attached to said substrate, said photoactivatable silane comprising the formula PG-LS-SN wherein PG is a photoactivatable group for photochemically crosslinking, LS is a linkage and spacer group, and SN is a silane group said substrate attached to said photoactivatable silane compound through said silane group, a functionalized polymer having reactive functionalized groups attached to said photoactivatable silane compound via photochemical cross-linking of said functionalized polymer to said photoactivatable group through photoactivation of said photoactivatable group; and a plurality of biopolymers attached to said functionalized polymer through said reactive functional groups.

10. An array of biopolymers according to claim 9 wherein said photoactivatable group for photochemically crosslinking is hydrophobic and said functionalized polymer is hydrophilic.

11. An array of biopolymers according to claim 9 wherein said reactive functional groups are selected from the group consisting of hydroxyl, amino, carboxyl, thiol and amide.

12. An array of biopolymers according to claim 9 wherein said functionalized polymer is selected from the group consisting of polyvinyl alcohol, dextran, hydroxyethylcellulose, poly(2-hydroxylpropyl) methacrylate, 88% hydrolyzed polyvinyl alcohol, 80% ethoxylated plyethylenimine, poly(vinylalcohol-co-ethylene), hydrogenated poly(phenyl vinyl ketone), reduced poly-glutaldehyde, hydroxyethylacrylamide and 2-hydroxyethylacrylamide-methylacrylamide.

13. An array of biopolymers according to claim 9 wherein said photoactivatable group for photochemically crosslinking is selected from a group consisting of 14. An array of biopolymers according to claim 9 wherein said photoactivatable group comprises a photoreactive benzophenone.

15. An array of biopolymers according to claim 9 wherein said saline group comprises an activated silicon group.

16. An array of biopolymers according to claim 14 wherein said activated silicon group is capable of reacting with a functional group on said substrate.

17. An array of biopolymers according to claim 15 wherein said saline group is selected from a group consisting of 18. An array of biopolymers according to claim 9 wherein said LS group is selected from the group consisting of 19. An array of biopolymers according to claim 9 wherein said photoactivatable silane compound is 4-(3'-triethoxysily)propylamidobenzophenone or 4-(3'-triethoxysilyl)propyloxybenzophenone.

20. An array of biopolymers according to claim 9 wherein said substrate is glass.

21. An array of biopolymers according to claim 9 wherein said biopolymers are polynucleotides.

22. An array of biopolymers according to claim 20 wherein said polynucleotides are oligonucleotides.

23. An array of biopolymers according to claim 9 wherein said biopolymers are proteins.

24. An array of biopolymers according to claim 9 wherein said biopolymers are peptides.

25. A method of making an array of biopolymers comprising the steps of providing a substrate having a surface,
   silanating said surface of said substrate with a photoactivatable silane compound having the formula PG-LS-SN wherein PG is a photoactivatable group for photochemically crosslinking, LS is a linkage and spacer group, and SN is a silane group wherein said surface of said substrate is attached to said photoactivatable silane compound through said silane group;
   providing a functionalized polymer having reactive functionalized groups;
   photochemically crosslinking said photoactivatable silane compound with said functionalized polymer via photoactivation of said photoactivatable group; and
   attaching a plurality of biopolymers to said functionalized polymer via said reactive functionalized groups.

26. A method of making an array of biopolymers according to claim 25 wherein said photoactivatable group is a hydrophobic and said functionalized polymer is hydrophilic.

27. A method of making an array of biopolymers according to claim 25 wherein said functionalized polymer is selected from the group consisting of polyvinyl alcohol, dextran, hydroxyethylcellulose, poly(2-hydroxylpropyl) methacrylate, 88% hydrolyzed polyvinyl alcohol, 80% ethoxylated plyethylenimine, poly(vinylalcohol-co-ethylene), hydrogenated poly(phenyl vinyl ketone), reduced poly-glutaldehyde, hydroxyethylacrylamide and 2-hydroxyethylacrylamide-methylacrylamide.

28. A method of making an array of biopolymers according to claim 25 wherein said saline group comprises an activated silicon group.

29. A method of making an array of biopolymers according to claim 25 wherein said activated silicon group is capable of reacting with a functional group on said surface of said substrate.

30. A method of making an array of biopolymers according to claim 25 wherein said synthesizing said plurality of biological polymer on said functionalized polymer requires an activation of said functionalized polymer.

31. A method of making an array of biopolymers according to claim 25 wherein said biopolymer is a nucleic acid.

32. A method of making an array of biopolymers according to claim 31 wherein said nucleic acid is an oligonucleotide.

33. A method of making an array of biopolymers according to claim 25 wherein said biopolymer is a protein.

34. A method of making an array of biopolymers according to claim 25 wherein said biopolymer is a peptide.

35. A method of making an array of biopolymers according to claim 25 wherein said array of biopolymers is synthesized in situ using a photolithographic method or a reagent deposition method.

36. A method of making an array of biopolymers according to claim 25 wherein said ray of biopolymers is synthesized in situ using an inkjet printing method.

37. A method of making an array of biopolymers according to claim 25 wherein said array of biopolymers is synthesized by spotting the biopolymer onto the functionalized polymer.

38. A method of making an array of biopolymers according to claim 25 wherein said photoactivatable group is selected from a group consisting of -continued
and

39. A method of making an array of biopolymers according to claim 25 wherein said photoactivatable group comprises a photoreactive benzophenone.

40. A method of making an array of biopolymers according to claim 25 wherein said saline group comprises an activated silicon group.

41. A method of making an array of biopolymers according to claim 25 wherein said activated silicon group is capable of reacting with a functional group on said substrate.

42. A method of making an array of biopolymers according to claim 25 wherein said saline group is selected from a group consisting of and 43. A method of making an array of biopolymers according to claim 25 wherein said LS group is selected from the group consisting of and 44. A method of making an array of biopolymers according to claim 25 wherein said photoactivatable silane compound is 4-(3'-triethoxysily)propylamidobenzophenone or 4-(3'-triethoxysilyl)propyloxybenzophenone.

45. A method of making an array of biopolymers according to claim 25 wherein said substrate is glass.

* * * * *